(12) United States Patent
Kamachi et al.

(10) Patent No.: US 7,374,682 B2
(45) Date of Patent: May 20, 2008

(54) METHOD AND APPARATUS FOR THE METHANE FERMENTATION TREATMENT OF WASTEWATER CONTAINING SULFUR COMPOUND

(75) Inventors: Kazumasa Kamachi, Tokyo (JP); Yasuhiro Honma, Tokyo (JP); Toshihiro Tanaka, Tokyo (JP); Toshio Tsukamoto, Tokyo (JP)

(73) Assignee: Ebara Corporation, Tokyo (JP)

( * ) Notice: Subject to any disclaimer, the term of this patent is extended or adjusted under 35 U.S.C. 154(b) by 28 days.

(21) Appl. No.: 10/551,818

(22) PCT Filed: Mar. 29, 2004

(86) PCT No.: PCT/JP2004/004403

§ 371 (c)(1),
(2), (4) Date: Jun. 22, 2006

(87) PCT Pub. No.: WO2004/096720

PCT Pub. Date: Nov. 11, 2004

(65) Prior Publication Data

US 2006/0243660 A1   Nov. 2, 2006

(30) Foreign Application Priority Data

Mar. 31, 2003 (JP) .............................. 2003-094373

(51) Int. Cl.
*C02F 3/28* (2006.01)
*C02F 1/72* (2006.01)
*C02F 1/78* (2006.01)

(52) U.S. Cl. ................. 210/603; 210/631; 210/916

(58) Field of Classification Search ................ 210/603, 210/630, 631, 916, 758–760, 143, 198.1, 210/259

See application file for complete search history.

(56) References Cited

U.S. PATENT DOCUMENTS

| | | | | |
|---|---|---|---|---|
| 3,388,057 A | * | 6/1968 | Callahan | 210/603 |
| 5,958,238 A | * | 9/1999 | Langerwerf | 210/603 |
| 5,976,373 A | * | 11/1999 | Trocciola et al. | 210/603 |
| 6,423,229 B1 | * | 7/2002 | Mao | 210/603 |

FOREIGN PATENT DOCUMENTS

JP         51-90163         8/1976

(Continued)

OTHER PUBLICATIONS

Tsuyoshi Imai et al., entitled "*Air Stripping—Thermophilic UASB Process for the Treatment of Evaporator Condensate from a Kraft Pulp Mill*", The 5th Symposiuim Journal by Japan Society on Water Environment, Sep. 26, 2002, pp. 145-146.

(Continued)

*Primary Examiner*—Fred Prince
(74) *Attorney, Agent, or Firm*—Wenderoth, Lind & Ponack, L.L.P.

(57) ABSTRACT

A method and apparatus for the anaerobic methane fermentation treatment of a wastewater containing a sulfur compound. An oxidizing agent is added to an organic wastewater to oxidize the sulfur compound contained therein to molecular sulfur before the anaerobic treatment step. The wastewater is then introduced into the anaerobic treatment step for the methane fermentation treatment thereof. The amount of the oxidizing agent to be added to the wastewater is controlled using as an indicator the concentration of the residual oxidizing agent in the water flowing into the anaerobic treatment step and/or the concentration of hydrogen sulfide in a biogas generated. The oxidizing agent may be ozone, hydrogen peroxide, sodium hypochlorite or a bromine based oxidizing agent. When the concentration of hydrogen sulfide in a biogas generated in the anaerobic treatment step is used as said indicator, the oxidizing agent may be suitably added such that the concentration of hydrogen sulfide is 3% or less.

4 Claims, 10 Drawing Sheets

FOREIGN PATENT DOCUMENTS

| JP | 1-207187 | 8/1989 |
| JP | 4-341388 | 11/1992 |
| JP | 10-156385 | 6/1998 |
| JP | 10-249383 | 9/1998 |
| JP | 11-689 | 1/1999 |
| JP | 2000-263084 | 9/2000 |
| JP | 2001-79590 | 3/2001 |
| JP | 2001-232388 | 8/2001 |
| JP | 2002-292377 | * 10/2002 |
| WO | 03/042116 | 5/2003 |

OTHER PUBLICATIONS

Yasuhiro Honma and Toshihiro Tanaka, entitled "*Methane Producing High Efficiency Energy-Saving Organic Wastewater Treatment System*", vol. 68, No. 12, Chemical Engineering Journal, published on Dec. 2004 (relevant portions: pp. 707-710).

Yasuhiro Honma; Kazumasa Kamachi and Toshihiro Tanaka, entitled "*Start up EGSB Reactor From Anaerobic Digester Sludge*", The 38th Symposium Journal by Japan Society on Water Environment, published on Mar. 2004 (relevant portions: p. 357).

Yasuhiro Honma; Toshihiro Tanaka and Kazumasa Kamachi, entitled "*Performance of EGSB Reactor in High SS Waste Water Treatment*", The 37th Symposium Journal by Japan Society on Water Environment, published on Mar. 2003 (relevant portions: p. 276).

Yasuhiro Honma; Toshihiro Tanaka and Masahiro Isaka, entitled "*Performance of the EGSB Reactor in High-Load Organic Wastewater Treatment*", The 36th Symposium Journal by Japan Society on Water Environment, published Mar. 2003 (relevant portions: p. 476).

Yasuhiro Honma; Toshihiro Tanaka and Yuichi Isozaki, entitled "*Performance of the EGSB Reactor in High-Load Organic Wastewater Treatment*", (Chemical Apparatus), published Mar. 2003 (relevant portions: Nos. 1 to 4).

Yasuhiro Honma, entitled *Performance of the EGSB Reactor in High-Load Organic Wastewater Treatment*, Vol. 27, No. 4, published Jan. 2002 (relevant portions: pp. 52-55).

Yasuhiro Honma; Toshihiro Tanaka; Susumu Adachi and Yuichi Isozaki, entitled "*Performance of the EGSB Reactor in High-Load Organic Wastewater Treatment*", No. 194, Ebara Journal, published Jan. 2002 (relevant portions: pp. 21-24).

Kazushi Yasuda, entitled "*Wastewater Treatment by High-Speed UASB Reactor*", Vol. 39, No. 7, Countermeasures for Environmental Resources, published 2003 (relevant portions: pp. 66-67).

Yuichi Isozaki, entitled "Performance of EGSB Reactor in High-Load Industrial Waste Water Treatment" (Industrial Machinery) published Jun. 2002, (relevant portions: pp. 17-19).

Sigeaki Numata and Souichi Shibuya, entitled "*Chemical Deodorization of the Foul Smelling Sulfur Compounds*", vol. 50, No. 2, Journal of Paper & Pulp Technology Association, published Feb. 1996 (relevant portions: pp. 40-45.

* cited by examiner

FIG. 7

| ELAPSED DAYS | CODCr VOLUME LOAD | | | | |
| --- | --- | --- | --- | --- | --- |
| | EMBODIMENT 1 | EMBODIMENT 2 | COMPARATIVE EXAMPLE 1 | COMPARATIVE EXAMPLE 2 | COMPARATIVE EXAMPLE 3 |
| 5 | 1 | 1 | 1 | 1 | 1 |
| 10 | 1 | 1 | 1 | 1 | 1 |
| 15 | 1 | 1 | 1 | 1 | 1 |
| 20 | 3 | 3 | 3 | 1 | 1 |
| 25 | 3 | 3 | 3 | 1 | 1 |
| 30 | 3 | 3 | 3 | 1 | 1 |
| 35 | 5 | 5 | 5 | 1 | 1 |
| 40 | 5 | 5 | 5 | 1 | 1 |
| 45 | 5 | 5 | 5 | 1 | 1 |
| 50 | 7 | 7 | 7 | 1 | 1 |
| 55 | 7 | 7 | 7 | 1 | 1 |
| 60 | 7 | 7 | 7 | 1 | 1 |
| 65 | 10 | 10 | 10 | 3 | 1 |
| 70 | 10 | 10 | 10 | 3 | 1 |
| 75 | 10 | 10 | 10 | 3 | 1 |
| 80 | 15 | 15 | 10 | 3 | 1 |
| 85 | 15 | 15 | 10 | 3 | 1 |
| 90 | 15 | 15 | 15 | 3 | 1 |
| 95 | 20 | 20 | 15 | 3 | 1 |
| 100 | 20 | 20 | 15 | 3 | 1 |
| 105 | 20 | 20 | 15 | 3 | 1 |
| 110 | 25 | 25 | 15 | 3 | 1 |
| 115 | 25 | 25 | 15 | 3 | 1 |
| 120 | 25 | 25 | 15 | 3 | 1 |
| 125 | 25 | 25 | 15 | 3 | 1 |
| 130 | 25 | 25 | 15 | 3 | 1 |
| 135 | 25 | 25 | 15 | 3 | 1 |
| 140 | 25 | 25 | 15 | 3 | 1 |
| 145 | 25 | 25 | 15 | 3 | 1 |
| 150 | 25 | 25 | 15 | 3 | 1 |

FIG.8

| ELAPSED DAYS | DISSOLVED SULFIDE CONCENTRATION | HYDROGEN SULFIDE CONCENTRATION IN BIOGAS | | | | |
|---|---|---|---|---|---|---|
| | RAW WATER | EMBODIMENT 1 | EMBODIMENT 2 | COMPARATIVE EXAMPLE 1 | COMPARATIVE EXAMPLE 2 | COMPARATIVE EXAMPLE 3 |
| 5 | 220 | 0.9 | 1.3 | 0.7 | 3 | 0.2 |
| 10 | 240 | 1 | 1.4 | 0.8 | 3.3 | 0.3 |
| 15 | 250 | 1 | 1.4 | 0.8 | 3.4 | 0.3 |
| 20 | 210 | 0.9 | 1.3 | 0.6 | 2.9 | 0.2 |
| 25 | 230 | 0.9 | 1.3 | 0.7 | 3.2 | 0.2 |
| 30 | 250 | 0.9 | 1.4 | 0.8 | 3.4 | 0.2 |
| 35 | 240 | 1 | 1.4 | 0.8 | 3.3 | 0.3 |
| 40 | 280 | 1 | 1.6 | 0.9 | 3.8 | 0.3 |
| 45 | 270 | 1 | 1.4 | 0.9 | 3.7 | 0.3 |
| 50 | 280 | 1 | 1.6 | 0.9 | 3.8 | 0.3 |
| 55 | 240 | 1 | 1.5 | 0.8 | 3.3 | 0.3 |
| 60 | 350 | 1 | 1.8 | 1.8 | 4.8 | 0.3 |
| 65 | 450 | 1 | 1.9 | 4.1 | 7.2 | 0.3 |
| 70 | 300 | 0.8 | 1.4 | 2.0 | 4.8 | 0.2 |
| 75 | 280 | 0.9 | 1.4 | 1.0 | 3.8 | 0.2 |
| 80 | 290 | 1 | 1.5 | 1.0 | 4.0 | 0.3 |
| 85 | 250 | 1 | 1.4 | 0.9 | 3.4 | 0.3 |
| 90 | 200 | 0.8 | 1.3 | 0.7 | 2.7 | 0.2 |
| 95 | 280 | 0.9 | 1.6 | 0.9 | 3.8 | 0.2 |
| 100 | 570 | 1 | 2.1 | 5.3 | 7.8 | 0.3 |
| 105 | 600 | 1 | 2.2 | 7.3 | 8.2 | 0.3 |
| 110 | 540 | 1 | 2 | 5.8 | 7.4 | 0.3 |
| 115 | 400 | 1 | 1.8 | 4.6 | 5.5 | 0.3 |
| 120 | 200 | 1 | 1.3 | 0.8 | 2.7 | 0.3 |
| 125 | 240 | 1 | 1.4 | 0.9 | 3.3 | 0.3 |
| 130 | 210 | 0.9 | 1.1 | 0.8 | 2.9 | 0.2 |
| 135 | 280 | 0.9 | 1.5 | 0.8 | 3.8 | 0.2 |
| 140 | 250 | 0.9 | 1.4 | 0.8 | 3.4 | 0.2 |
| 145 | 240 | 0.8 | 1.3 | 0.8 | 3.3 | 0.2 |
| 150 | 240 | 0.9 | 1.2 | 0.8 | 3.3 | 0.2 |

FIG.9

| ELAPSED DAYS | CODcr REMOVAL RATE | | | | |
|---|---|---|---|---|---|
| | EMBODIMENT 1 | EMBODIMENT 2 | COMPARATIVE EXAMPLE 1 | COMPARATIVE EXAMPLE 2 | COMPARATIVE EXAMPLE 3 |
| 5 | 85 | 85 | 84 | 83 | 80 |
| 10 | 85 | 85 | 82 | 75 | 67 |
| 15 | 90 | 90 | 86 | 33 | 30 |
| 20 | 84 | 84 | 86 | 20 | 15 |
| 25 | 86 | 86 | 84 | 16 | 10 |
| 30 | 91 | 91 | 87 | 15 | 8 |
| 35 | 84 | 84 | 82 | 12 | 7 |
| 40 | 88 | 88 | 87 | 11 | 9 |
| 45 | 89 | 89 | 88 | 13 | 8 |
| 50 | 80 | 80 | 82 | 12 | 7 |
| 55 | 85 | 85 | 83 | 11 | 9 |
| 60 | 88 | 88 | 80 | 10 | 10 |
| 65 | 79 | 79 | 55 | 9 | 9 |
| 70 | 86 | 86 | 60 | 9 | 7 |
| 75 | 87 | 87 | 63 | 7 | 9 |
| 80 | 77 | 77 | 75 | 8 | 6 |
| 85 | 85 | 85 | 80 | 7 | 7 |
| 90 | 86 | 86 | 72 | 9 | 7 |
| 95 | 75 | 75 | 70 | 6 | 7 |
| 100 | 80 | 80 | 19 | 7 | 8 |
| 105 | 82 | 82 | 12 | 7 | 5 |
| 110 | 76 | 76 | 15 | 8 | 5 |
| 115 | 78 | 78 | 14 | 5 | 8 |
| 120 | 75 | 75 | 19 | 6 | 5 |
| 125 | 77 | 77 | 20 | 5 | 4 |
| 130 | 80 | 80 | 24 | 8 | 6 |
| 135 | 78 | 78 | 30 | 5 | 5 |
| 140 | 75 | 75 | 28 | 4 | 4 |
| 145 | 74 | 74 | 39 | 6 | 6 |
| 150 | 78 | 78 | 44 | 5 | 6 |

FIG.10

| ELAPSED DAYS | RESIDUAL CHLORINE CONCENTRATION | |
|---|---|---|
| | EMBODIMENT 2 | COMPARATIVE EXAMPLE 3 |
| 5 | 0.9 | 0.0 |
| 10 | 1 | 0.0 |
| 15 | 1 | 0.0 |
| 20 | 0.9 | 0.0 |
| 25 | 0.9 | 0.0 |
| 30 | 0.9 | 0.0 |
| 35 | 1 | 0.0 |
| 40 | 1 | 0.0 |
| 45 | 1 | 0.0 |
| 50 | 1 | 0.0 |
| 55 | 1 | 0.0 |
| 60 | 1 | 0.0 |
| 65 | 1 | 0.1 |
| 70 | 0.8 | 0.0 |
| 75 | 0.9 | 0.0 |
| 80 | 1 | 0.0 |
| 85 | 1 | 0.0 |
| 90 | 0.8 | 0.0 |
| 95 | 0.9 | 0.0 |
| 100 | 1 | 0.1 |
| 105 | 1 | 0.1 |
| 110 | 1 | 0.1 |
| 115 | 1 | 0.1 |
| 120 | 1 | 0.0 |
| 125 | 1 | 0.0 |
| 130 | 0.9 | 0.0 |
| 135 | 0.9 | 0.0 |
| 140 | 0.9 | 0.0 |
| 145 | 0.8 | 0.0 |
| 150 | 0.9 | 0.0 |

METHOD AND APPARATUS FOR THE METHANE FERMENTATION TREATMENT OF WASTEWATER CONTAINING SULFUR COMPOUND

TECHNICAL FIELD

The present invention relates to a methane fermentation treatment of a wastewater containing a sulfur compound. More particularly, the present invention is directed to a method and apparatus for the methane fermentation treatment of an organic wastewater discharged from various factories such as paper mill factories and chemical factories and containing a sulfur compound such as hydrogen sulfide or methyl mercaptan.

BACKGROUND ART

A methane fermentation treatment method in which an organic wastewater or an organic waste is decomposed by methane fermentation is superior with respect to energy savings as compared with an aerobic treatment such as an active sludge process, because it does not require an energy for aeration, it produces little surplus sludge and it permits energy recovery from a biogas generated. However, since the amount of proliferation of methane producing bacteria or methane fermentation bacteria is small and since sedimentation efficiency thereof is not high, the bacteria are apt to be discharged together with the treated water. Therefore, it is difficult to increase the concentration of bacteria within a fermentation reactor used for the methane fermentation treatment. Further, the methane fermentation treatment method has a problem with respect to costs and sites.

When a sulfur-containing waste water from a craft pulp cooking step, which contains sulfur-based foul odor substances, such as hydrogen sulfide and methyl mercaptan, that will hinder the methane fermentation, is treated by a medium temperature methane fermentation process using an anaerobic sludge blanket method, it is necessary to remove such foul odor substances and organic matters by steam stripping or air stripping. Thus, the above method has a problem because of increased operation costs.

Also known is a method which includes adding an agent for inhibiting the formation of hydrogen sulfide to a sulfate-containing organic wastewater, in which hydrogen sulfide has been formed, to produce a sulfide. The thus formed sulfide is then precipitated and removed from the wastewater. In the above method, the hydrogen sulfide is precipitated and removed as a sulfide formed by a heavy metal contained in the agent for inhibiting the formation of hydrogen sulfide. This method, however, has a problem, for example, that the methane fermentation is hindered by the heavy metal which is contained in the agent for inhibiting the formation of hydrogen sulfide which has been added in an excessive amount to the wastewater.

Thus, the conventional anaerobic active sludge treatment method for wastewater, such as chemical industry waste water (e.g. paper and pulp industry effluent), containing sulfur compounds, for example, hydrogen sulfide and methyl mercaptan, in high concentrations has the following problems.

(1) When a sulfur-containing organic substance is anaerobically decomposed, hydrogen sulfide is generated. When the pH is lowered, non-dissociable hydrogen sulfide, namely molecular hydrogen sulfide is generated. Such molecular hydrogen sulfide hinders methane fermentation.

(2) The excessive addition of the agent for removing hydrogen sulfide not only increases the process costs but also greatly damages anaerobic bacteria, when streaming in the methane fermentation reactor.

It is an object of the present invention to provide a high performance anaerobic methane fermentation treatment method and apparatus which can solve the problems of the above-described conventional technique and which can be applied to a sulfur compound-containing wastewater.

DISCLOSURE OF INVENTION

To solve the above problem, the present invention provides a method for the methane fermentation treatment of an organic wastewater containing a sulfur compound, in that an oxidizing agent is added, prior to an anaerobic treatment step, to the organic wastewater to oxidize the sulfur compound contained therein to molecular sulfur, the resulting organic wastewater being introduced into the anaerobic treatment step and subjected to methane fermentation treatment, and in that the amount of the oxidizing agent to be added to the wastewater is controlled using as an indicator the concentration of the residual oxidizing agent in the water flowing into the anaerobic treatment step and/or the concentration of hydrogen sulfide in a biogas generated. As used herein, the languages "the concentration of the oxidizing agent and/or the concentration of hydrogen sulfide in a biogas generated" are intended to refer to at least one of the concentration of the oxidizing agent and the concentration of hydrogen sulfide in the biogas generated.

In the above treatment method, at least one member selected from ozone, hydrogen peroxide, sodium hypochlorite and a bromine based oxidizing agent may be used as the oxidizing agent. When the concentration of hydrogen sulfide in a biogas generated in the anaerobic treatment step is used as the indicator, the oxidizing agent is preferably added such that the concentration of hydrogen sulfide is 3% or less. When the concentration of the residual oxidizing agent is used as the indicator, the oxidizing agent may be added on the basis of at least one of the indicated values selected from the residual ozone concentration, the residual hydrogen peroxide concentration, the residual chlorine concentration and the residual bromine concentration in the wastewater and the oxidation and reduction potential of the waste water.

The present invention also provides an apparatus for the methane fermentation treatment of an organic wastewater containing a sulfur compound, comprising an oxidation reactor in which an oxidizing agent is added to the organic wastewater and is reacted therewith, and a methane fermentation reactor in which the waste water which has been subjected to the oxidation treatment is subjected to a methane fermentation treatment, wherein the methane fermentation reactor is provided with means for measuring the concentration of the residual oxidizing agent in the water flowing into the reactor and/or means for measuring the concentration of hydrogen sulfide in a gas generated in the methane fermentation reactor, and control means for controlling the amount of the oxidizing agent added to be on the basis of the measured value. As used herein, the languages "means for measuring the concentration of the residual oxidizing agent and/or means for measuring the concentration of hydrogen sulfide in a gas generated in the reactor" are intended to refer to at least one of the both means.

This application is based on the Patent Application No. 2003-094373 filed on Mar. 31, 2003 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

BRIEF DESCRIPTION OF DRAWINGS

FIG. 7 is a drawing in the form of a table, showing the results of the experiments in Example 1;

FIG. 8 is a drawing in the form of a table, showing changes of the dissolved sulfide concentration and changes of the hydrogen sulfide concentration in a biogas;

FIG. 9 is a drawing in the form of a table, showing changes of the result of the COD treatment; and FIG. 10 is a drawing in the form of a table, showing changes of the residual chlorine concentration.

BEST MODE FOR CARRYING OUT THE INVENTION

The present invention will be described in detail below.

The anaerobic treatment according to the present invention includes a methane fermentation treatment. Such a treatment may be an anaerobic treatment in which whole organic substances are charged and digested or a high load anaerobic treatment, such as an upflow sludge blanket method, a fluidized bed method or a packed bed method, in which soluble substances are subjected to an anaerobic treatment. Either method may be suitably used. The anaerobic treatment may be carried out using a single reactor system in which the acid fermentation and methane fermentation are performed in one reactor or a dual reactor system in which both reactions are performed in separate reactors.

Figure 1:
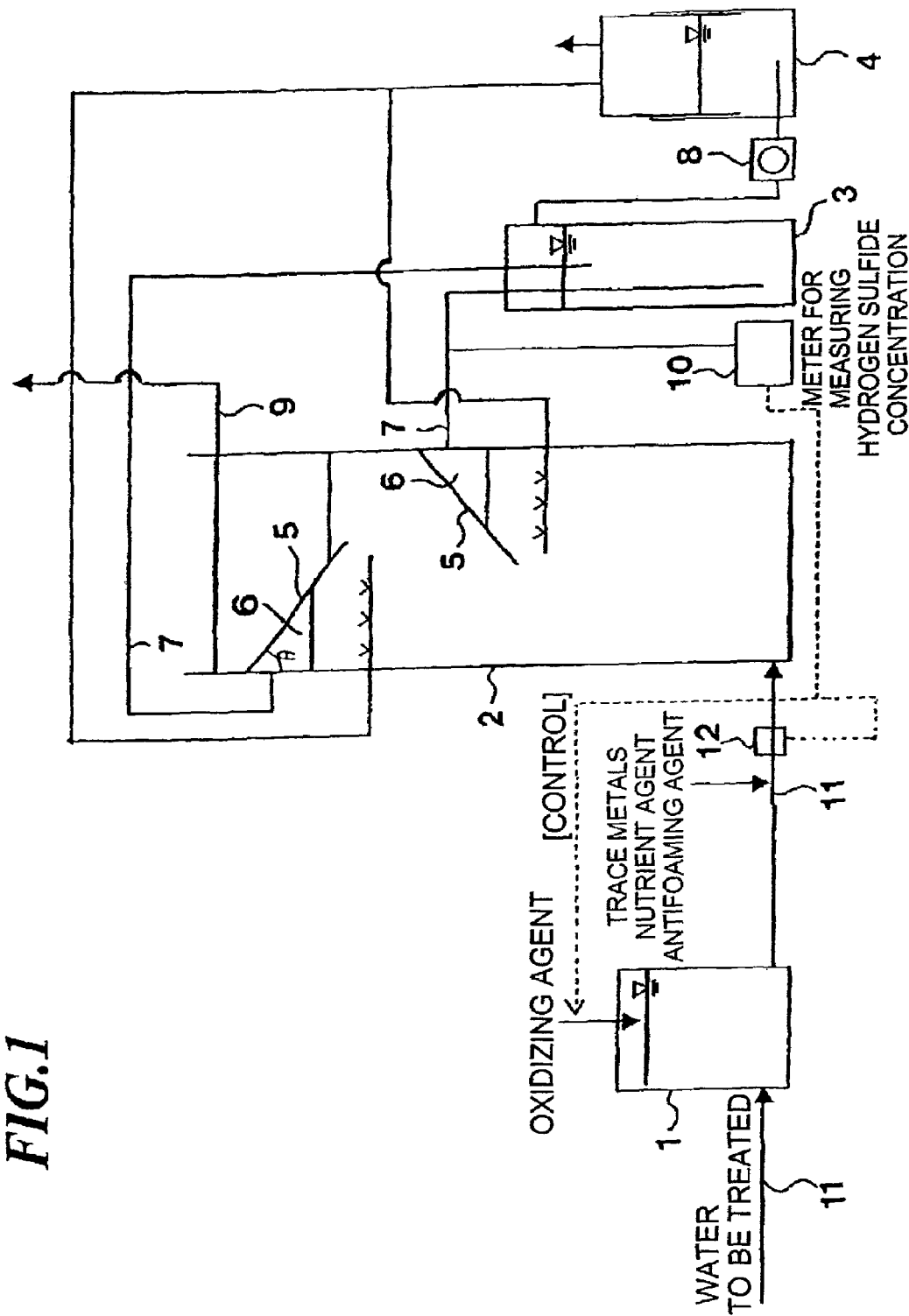
FIG. 1 is a flow diagram, showing an example of a methane fermentation apparatus according to one embodiment of the present invention.

FIG. 1 illustrates a flow diagram, showing an example of an upflow anaerobic methane fermentation treatment apparatus according to the present invention which is preferably used to carry out the methane fermentation treatment method.

In FIG. 1, designated as 1 is an oxidation reactor, 2 a methane fermentation reactor (reactor), 3 a water-sealed tank, 4 a gas holder, 5 a baffle plate, 6 a gas phase section, 7 a pipe for collecting a gas generated, 8 a gas meter, 9 a pipe for treated water, 10 a meter for measuring hydrogen sulfide concentration, 11 a raw water feed pipe, and designated as 12 is a device for measuring residual oxidizing agent.

Referring to FIG. 1, the reactor 2 with which the raw water feed pipe 11 is in fluid communication has a tubular shape and has closed upper and lower ends. Each of the left and right side walls of the reactor 2 is provided with the baffle plate 5. The baffle plates 5 have one end portions fixed to respective side walls and extend downward with the other end portions thereof facing opposite side walls. The baffle plates 5 are vertically spaced from each other and extend in opposite directions from two, left and right side walls. Each gas phase section 6, which collects a gas when the reaction starts to generate it, is provided with a discharge port in communication with the pipe 7 for collecting the gas generated.

Each of the pipes 7 connected to the gas phase sections 6 for collecting the generated gas extends into the water filled in the water-sealed tank 3 and opens in its discharge end. The open ends of the pipes are positioned at suitable depths of different water pressures. The gas meter 8 is connected to the water-sealed tank 3 for measuring the flow rate of the gas discharged through the generated gas collecting pipes 7. The gas holder 4 is disposed downstream of the gas meter 8. The reactor 2 has an upper part provided with an opening to which the pipe 9 for the treated water is connected to discharge the supernatant liquid. The meter 10 for measuring hydrogen sulfide concentration is provided at a position between the gas phase section 6 and the water-sealed tank 3.

The reactor 2 is used after granular sludge containing anaerobic bacteria has been charged. The anaerobic treatment at which the present invention is aimed may encompass anaerobic treatments performed at a temperature range of a medium temperature methane fermentation treatment whose suitable temperature is 30° C. to 35° C. and a high temperature methane fermentation treatment whose suitable temperature is 50° C. to 55° C. The granular sludge containing anaerobic bacteria is introduced in the reactor 2 to which the water to be treated is fed through the raw water feed pipe 11. The water to be treated may be diluted, if necessary, with the recycled treated water or diluting water supplied from outside. The feed of the water to be treated is controlled so that the flow rate of the water feed in the reactor is 0.5 to 5 m/h.

In the ordinary methane fermentation, an acid fermentation reactor is provided upstream of a methane fermentation reactor. In the present treatment method, the oxidization reactor 1 may be provided upstream of the acid fermentation reactor or between the acid fermentation reactor and the methane fermentation reactor. However, the oxidization reactor 1 is preferably provided between the acid fermentation reactor and the methane fermentation reactor, since hydrogen sulfide is generated by the reduction of sulfate ions in the acid fermentation reactor. If desired, the oxidation reactor 1 may be omitted and, instead, the oxidizing agent may be directly injected into the pipe.

By adding a trace amount of metals such as Fe, Co and Ni, to the water to be treated, the methane-forming bacteria may be activated so that the granule formation efficiency may be improved. The trace metals are desirably added at a position between the oxidation reactor and the methane fermentation reactor, since they can react with hydrogen sulfide in water to form sulfides having a small solubility and thereby to reduce bioavailability.

The oxidizing agent added to the oxidization reactor 1 is desirably such that it does not adversely affect the succeeding methane fermentation and, for this reason, is preferably ozone, hydrogen peroxide, sodium hypochlorite or a bromine-based oxidizing agent.

When the additive amount of the oxidizing agent is excessively large, not only the costs increase but also the growth of anaerobic bacteria used in the later stage is inhibited. Therefore, the amount of the oxidizing agent is suitably such that at least one of the residual ozone concentration, residual hydrogen peroxide concentration, residual chlorine concentration and residual bromine concentration in the waste water at the exit of the oxidation reactor is 0.5 mg/L or less, preferably 0.1 mg/L or less, more preferably non-detectable. When the oxidation and reduction potential is used as the indicator, the potential is +100 mV or below, preferably zero mV or below, more preferably −200 mV or below. Particularly, in the oxidation of hydrogen sulfide, it is not preferable that sulfur components which have been oxidized to molecular sulfur are further oxidized into sulfate ions, because sulfuric acid reduction takes place in the anaerobic treatment step.

When the concentration of sulfur compounds in the wastewater is relatively stable, the oxidizing agent may be added in a constant amount. When the concentration of sulfur compounds in the wastewater significantly varies, however, it is necessary to add the oxidizing agent in a controlled amount. Thus, the oxidizing agent is added under a control so that the time lag between the addition timing of the oxidizing agent and the occurrence of a change of the concentration of the oxidizing agent in the wastewater is minimized. It is advisable that the control be done on the basis of the residual chlorine concentration in the fermentation reactor or the value indicated by the indicating instrument 12 of the oxidation and reduction potential. In the method according to the present invention, the addition of the oxidizing agent may be controlled using, as the indicator, the hydrogen sulfide concentration in a biogas generated during the anaerobic treatment, since the hydrogen sulfide concentration in the gas varies corresponding to the concentration of the oxidizing agent in the aqueous phase. The controlled addition may be made using any one of the above indicators or using two or more of the indicators in combination.

In order to determine the optimum addition amount, the oxidizing agent may be suitably added such that the hydrogen sulfide concentration detected by the above-described hydrogen sulfide concentration meter is maintained at 3% or less, preferably 1.5% or less, more preferably 1% or less. When the hydrogen sulfide concentration in the generated gas is not more than 1%, no inhibition of the methane fermentation by molecular hydrogen sulfide occurs.

EMBODIMENTS

The present invention will be described concretely below by way of embodiments.

Embodiments 1 and 2 and Comparative Examples 1, 2 and 3

Embodiment 1 represents a method in which an oxidizing agent is added to raw water so as to control the concentration of hydrogen sulfide in a biogas to 1% or less, while Embodiment 2 represents a method in which an oxidizing agent is added to the raw water so as to control the concentration of residual chlorine at an outlet of an oxidization reactor to 0.1 mg/L or less. In the both embodiments, the oxidizing agent was controlled to be added. Comparative Example 1 is a method in which the concentration of hydrogen sulfide in a biogas is assumed to be 4% and in which an oxidizing agent is continuously added at a given constant rate to reduce the hydrogen sulfide concentration to 1% or less. Comparative Example 2 is a method in which no oxidizing agent is added. Comparative Example 3 represents a method in which an oxidizing agent is added so as to control the concentration of residual bromine at an outlet of an oxidization reactor to 1.0 mg/L or less. Sodium hypochlorite was used as the oxidizing agent in each of Embodiments and Comparative Examples.

A wastewater containing a high sulfur content was treated with an apparatus of the present invention as shown in FIG. 1.

In Embodiments, the oxidizing agent was added to the water to be treated in the oxidization reactor 1 disposed upstream of the methane fermentation reactor 2, to which Fe, Ni and Co were thereafter added. The resulting water was then fed to the methane fermentation reactor 2. In Comparative Examples, there was not provided the oxidation reactor 1. Fe, Ni, Co were added in a preparation vessel and the resulting water was thereafter fed to the methane fermentation reactor.

The reactor had a volume of 3 $m^3$. The amount of the generated gas collected in each of the gas phase sections 6 was measured with the gas meter 8 connected to the water-sealed tank 8. A temperature control was made to maintain the temperature of the water in the reactor 2 at 35° C. In Embodiments, the hydrogen sulfide concentration meter 10 was provided between the lowermost gas phase section 6 and the water-sealed tank 3.

The raw water used was a wastewater (main ingredient: methanol, CODcr: 7,000-10,000 mg/L, dissolved sulfides: 100-600 mg/L) to which inorganic nutrient salts containing elements such as nitrogen and phosphorus had been added.

A portion of the treated water was introduced, as a recycled liquid, into the reactor together with the raw water so that the water feed rate was adjusted to 2 m/h. The proportion of the flow rate of the raw water relative to the amount of the recycled treated water was set in correspondence to the COD load.

Figure 2:
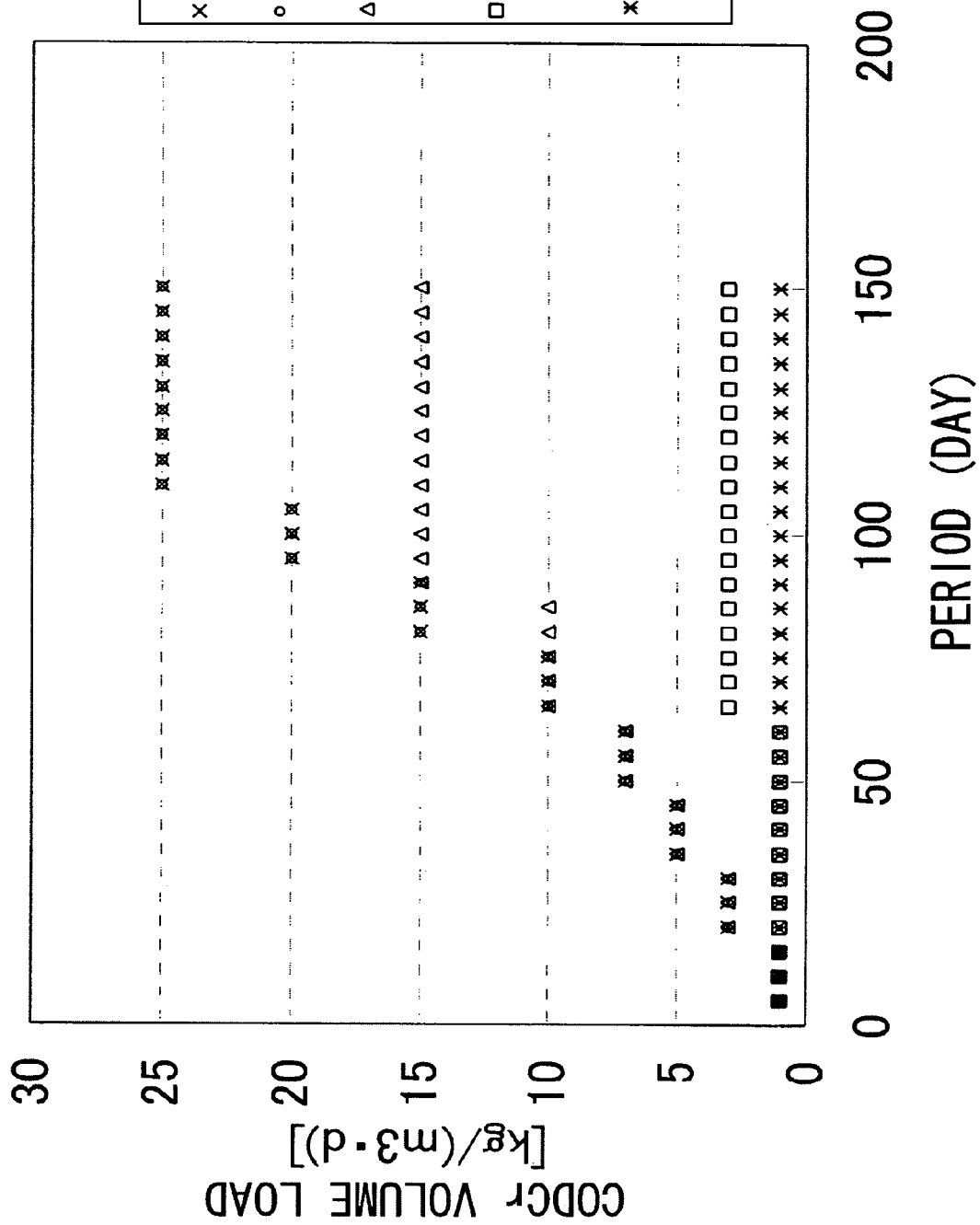
FIG. 2 is a graph, showing the results of the experiments of Example 1.
Figure 3:
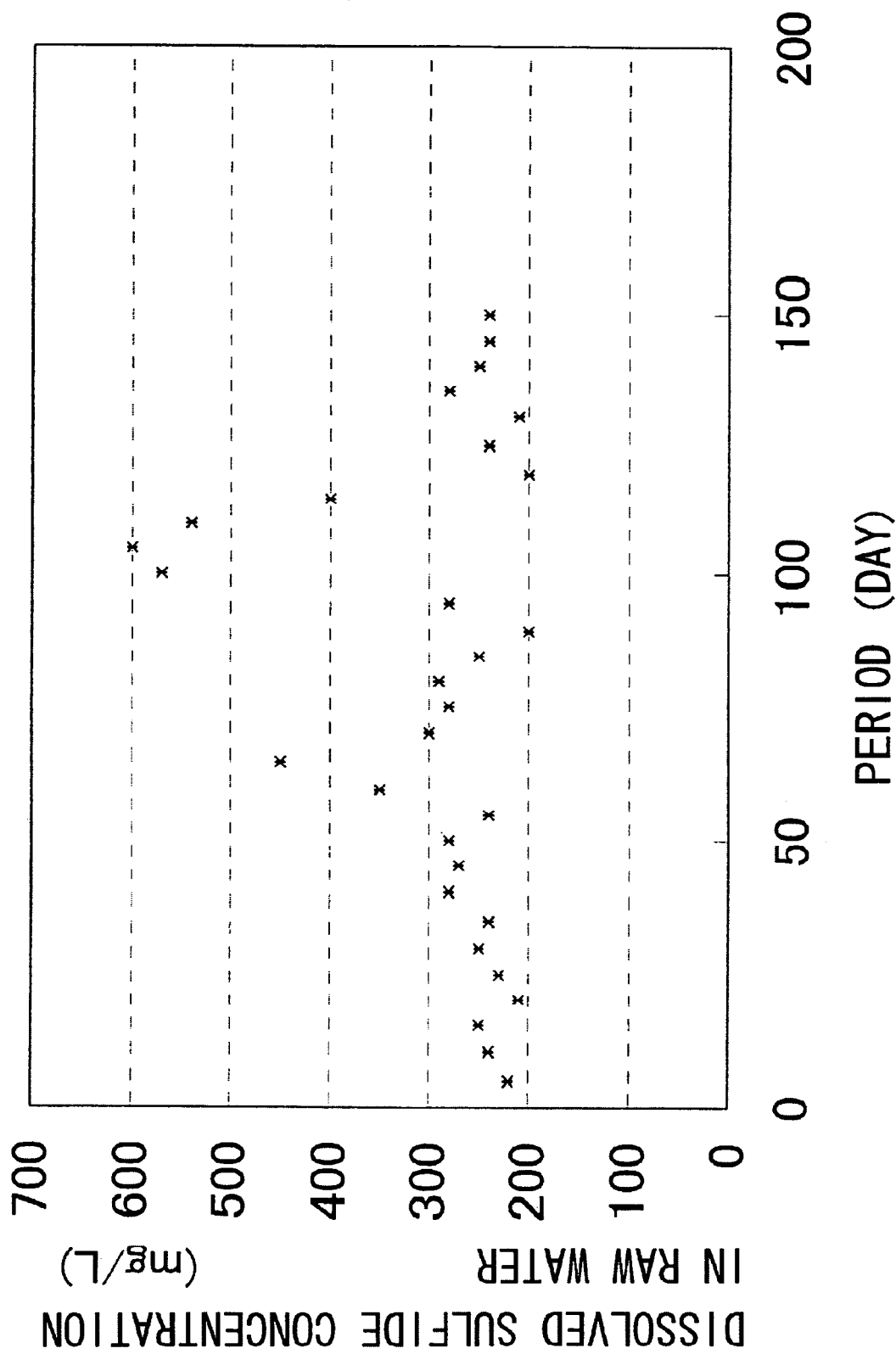
FIG. 3 is a graph, showing changes of the dissolved sulfide concentration in raw water.
Figure 4:
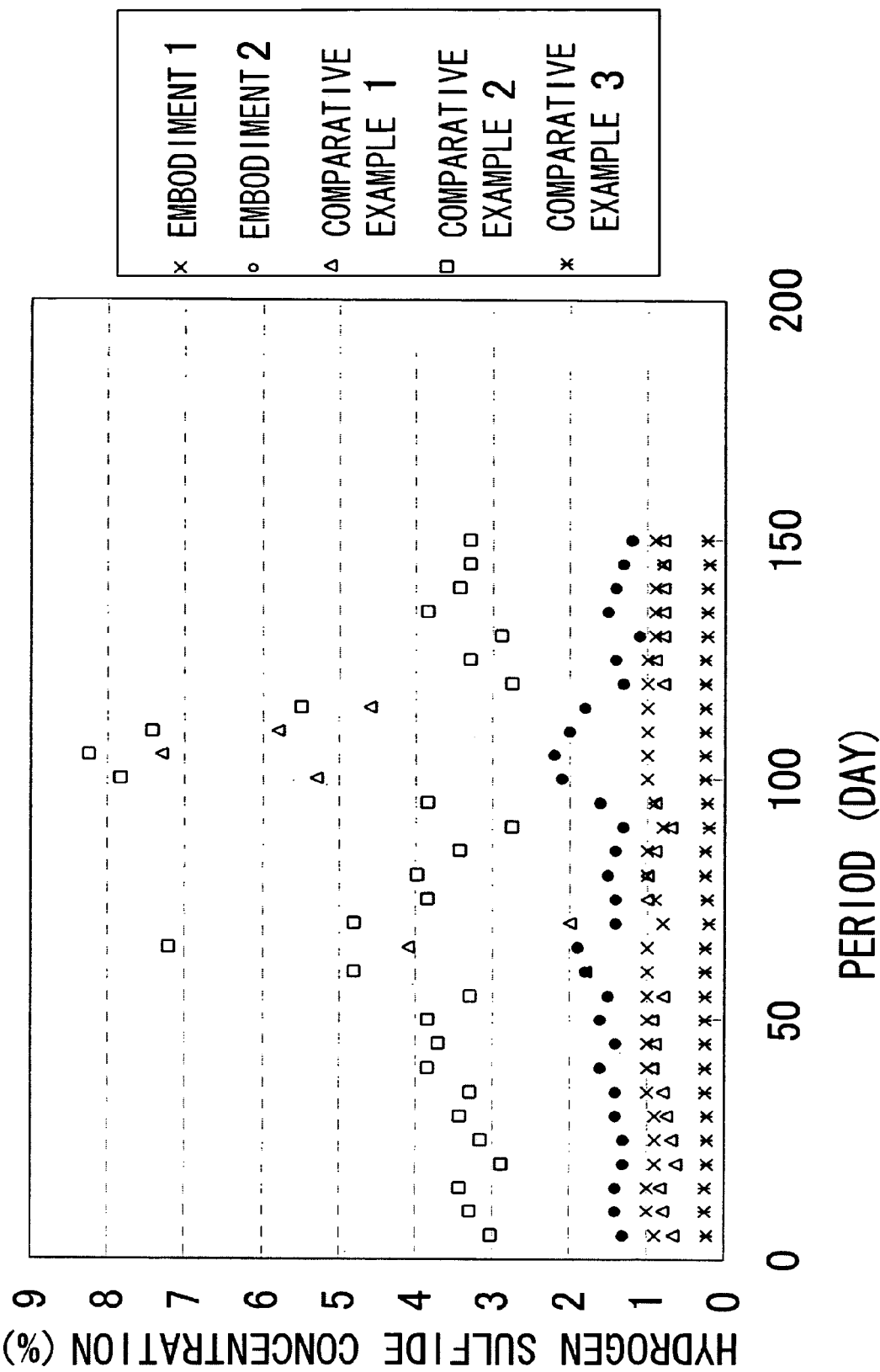
FIG. 4 is a graph, showing changes of the hydrogen sulfide concentration in a biogas.
Figure 5:
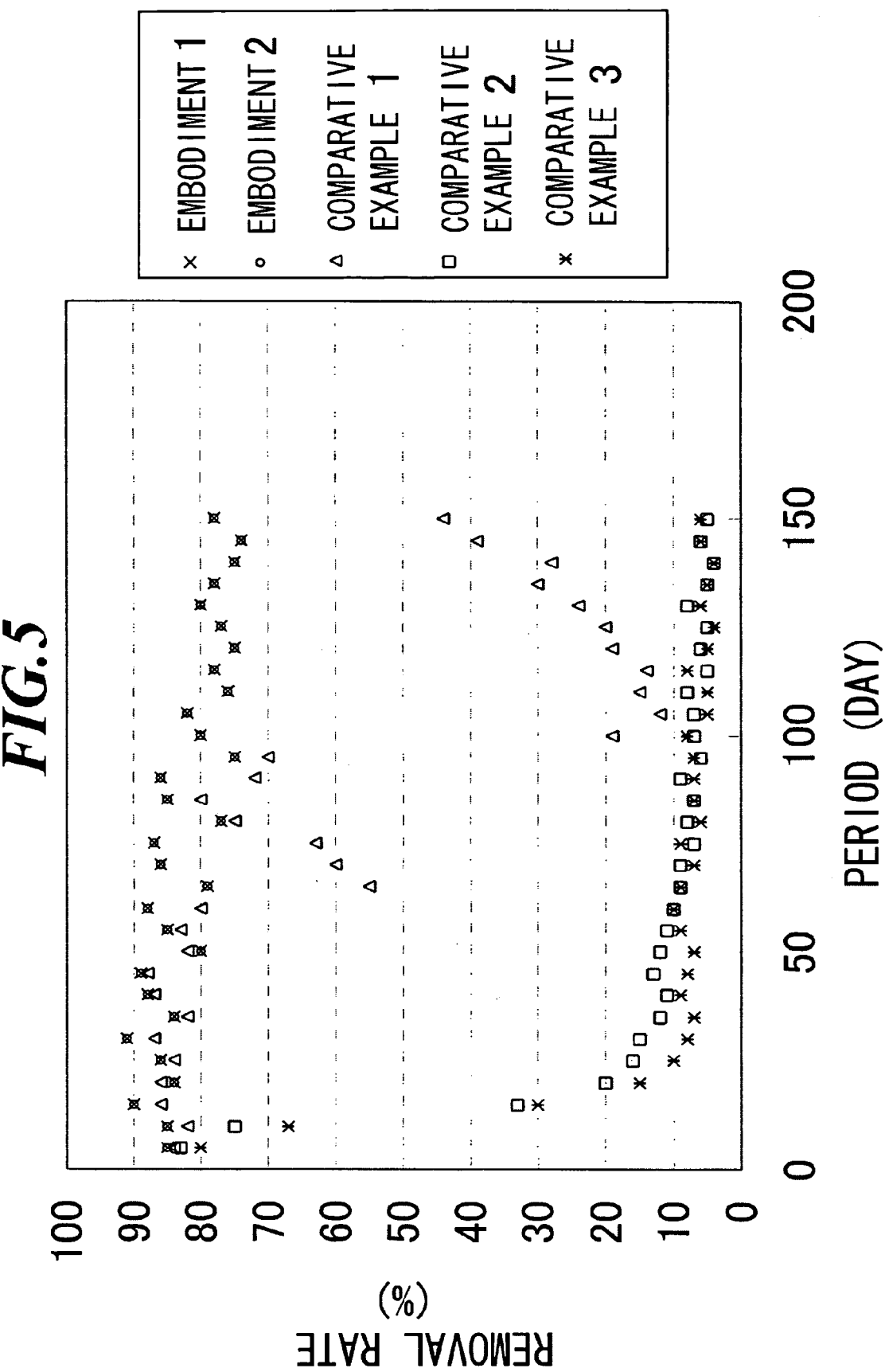
FIG. 5 is a graph, showing changes of the result of the COD treatment.
Figure 6:
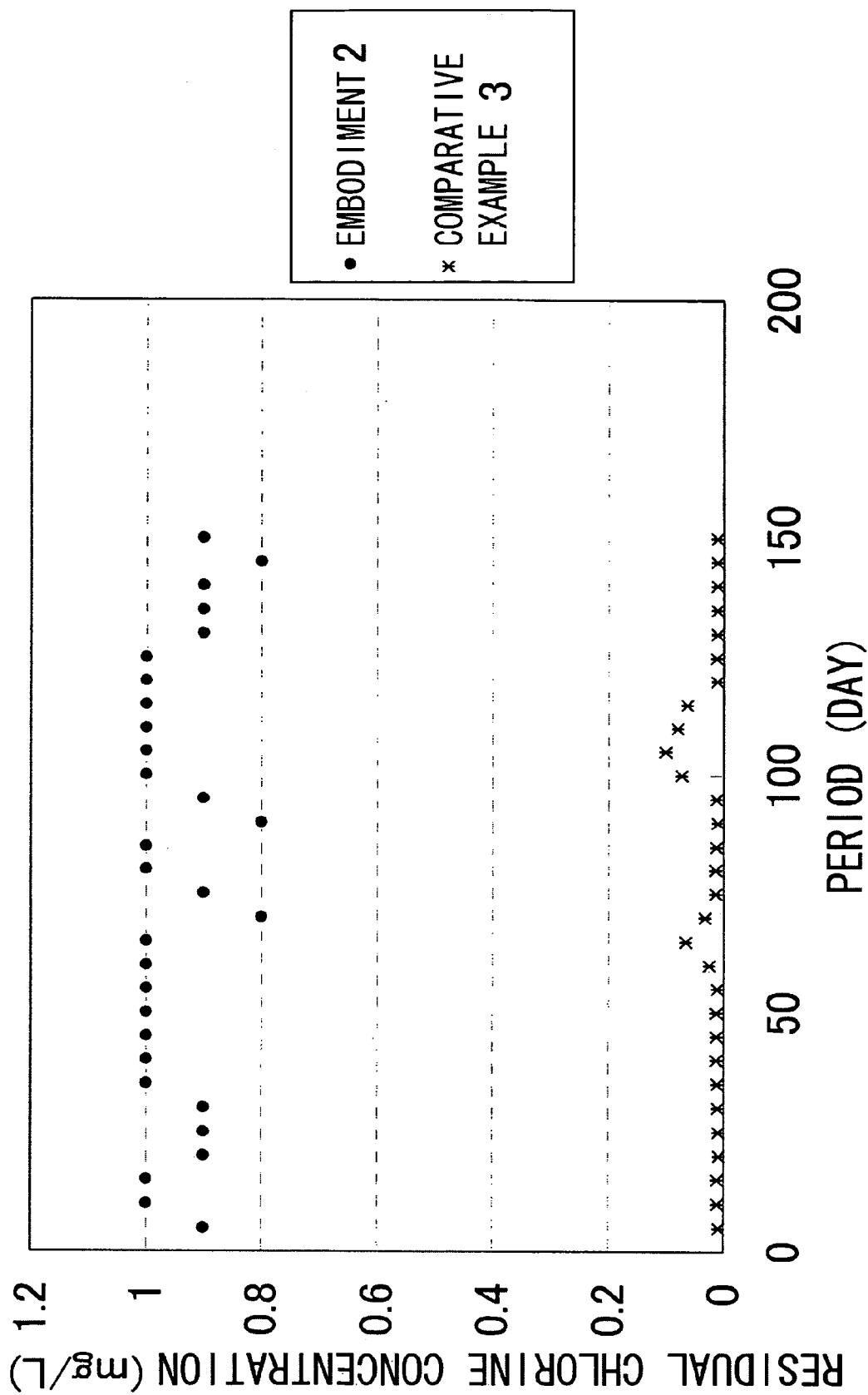
FIG. 6 is a graph, showing changes of the residual chlorine concentration.

By way of graphs, FIG. 2 illustrates the progresses of experiments, FIG. 3 illustrates changes of the concentration of the dissolved sulfides in the raw water, FIG. 4 illustrates the concentration of hydrogen sulfide in the biogas, FIG. 5 illustrates changes of the result of the COD treatment and FIG. 6 illustrates changes of residual chlorine concentration. In each of the series, the organic loading was gradually increased while taking the CODcr concentration of the treated water in consideration.

FIG. 7 to FIG. 10 are tables, both showing the values corresponding to FIG. 2 to FIG. 6.

In Embodiments 1 and 2, the CODcr removal rate of 78% was able to be achieved at CODcr volume loading of 25 kg/($m^3$·d).

In Comparative Example 1, on the other hand, when the concentration of the dissolved sulfides in the raw water increased to cause the concentration of the hydrogen sulfide to exceed 4% in the biogas, the CODcr removal rate decreased to about 10%. In Comparative Examples 2 and 3, the removal rate was low and CODcr was hardly removed. Thus, the removal rate was about 10%. The method of the present invention was able to provide a higher CODcr removal rate.

As have been described in the foregoing, there is known an upflow anaerobic sludge blanket process (hereinafter referred to as UASB) as a high efficiency fermentation reactor using a high bacteria concentration. This process has a merit that the concentration of methane producing bacteria in the reactor can be maintained at a high level because anaerobic bacteria such as methane producing bacteria may be granulated into granules. Thus, even when the concentration of organic matters in a wastewater is significantly high, this process permits a high efficiency treatment thereof.

However, when UASB treatment process is applied to the treatment of a wastewater having a high content of sulfur compounds (e.g. hydrogen sulfide and methyl mercaptan) such as a chemical industry wastewater (e.g. paper mill effluent or pulp industry wastewater), methane fermentation is adversely affected by the hydrogen sulfide contained in the raw water and the hydrogen sulfide formed in situ by anaerobic decomposition of the sulfur compounds. With the embodiments according to the present invention, such an adverse affection can be suppressed.

In the case of the medium temperature methane fermentation of a craft pulp wastewater using the upflow anaerobic sludge blanket process, a methanol-containing wastewater from a pulp cooking step is treated for the removal of its sulfur components. The resulting wastewater is mixed with a wastewater containing high molecular weight hydrocarbons and the mixture is fed to a methane fermentation reactor where the mixture is subjected to the methane fermentation.

In such a treatment process, it is necessary to subject the sulfur-containing wastewater from the craft pulp cooking step, which contains sulfur-based foul odor substances such as hydrogen sulfide and methyl mercaptan, to steam stripping or air stripping in order to remove the foul odor substances and organic substances. With the embodiments according to the present invention, it is possible to suppress the operation costs required for performing such a treatment.

INDUSTRIAL APPLICABILITY

In a method in which a wastewater containing a sulfur compound is treated for the oxidation of the sulfur compound prior to an anaerobic treatment step and is subsequently introduced into the anaerobic treatment step, the feeding rate of the oxidizing agent to be added is controlled such that the concentration of hydrogen sulfide in a biogas generated during the anaerobic treatment step is 3% or less. With such a method, high treatment performance is obtainable in a stable manner.

The invention claimed is:

1. A method for methane fermentation treatment of an organic wastewater containing a sulfur compound, comprising the steps of:
    adding an oxidizing agent to the organic wastewater to oxidize the sulfur compound contained therein to sulfur;
    subjecting the organic wastewater after the oxidizing step to an anaerobic treatment step for methane fermentation thereof; and
    controlling a feeding rate of the oxidizing agent to be added to the wastewater using a concentration of residual oxidizing agent in water flowing into the anaerobic treatment and/or a concentration of hydrogen sulfide in a biogas generated in the anaerobic treatment step as an indicator;
    wherein when the concentration of hydrogen sulfide in the biogas generated in the anaerobic treatment step is used as the indicator, the oxidizing agent is added such that the concentration of hydrogen sulfide is 3% or less.

2. The methane fermentation treatment as recited in claim 1, wherein at least one member selected from the group consisting of ozone, hydrogen peroxide, sodium hypochlorite and a bromine based oxidizing agent is used as the oxidizing agent.

3. A method for methane fermentation treatment of an organic wastewater containing a sulfur compound, comprising the steps of:
    adding an oxidizing agent to the organic wastewater to oxidize the sulfur compound contained therein to sulfur;
    subjecting the organic wastewater after the oxidizing step to an anaerobic treatment for methane fermentation thereof; and
    controlling a feeding rate of the oxidizing agent to be added to the wastewater using a concentration of residual oxidizing agent in water flowing into the anaerobic treatment step and/or a concentration of hydrogen sulfide in a biogas generated in the anaerobic treatment step as an indicator;
    wherein when the concentration of the residual oxidizing agent in the water flowing into the anaerobic treatment step is used as the indicator, the oxidizing agent is added on the basis of at least one indicated value selected from the group consisting of residual ozone concentration, residual hydrogen peroxide concentration, residual chlorine concentration, residual bromine concentration in the wastewater and oxidation-reduction potential of the waste water.

4. A method for methane fermentation treatment of an organic wastewater containing a sulfur compound, comprising the steps of:
    adding an oxidizing agent to the organic wastewater to oxidize the sulfur compound contained therein to sulfur;
    subjecting the organic wastewater after the oxidizing step to an anaerobic treatment for methane fermentation thereof; and
    controlling a feeding rate of the oxidizing agent to be added to the wastewater using a concentration of residual oxidizing agent in water flowing into the anaerobic treatment step and/or a concentration of hydrogen sulfide in a biogas generated in the anaerobic treatment step as an indicator;
    wherein at least one member selected from the group consisting of ozone, hydrogen peroxide, sodium hypochlorite and a bromine based oxidizing agent is used as the oxidizing agent; and
    wherein when the concentration of the residual oxidizing agent in the water flowing into the anaerobic treatment step is used as the indicator, the oxidizing agent is added on the basis of at least one indicated value selected from the group consisting of residual ozone concentration, residual hydrogen peroxide concentration, residual chlorine concentration, residual bromine concentration in the wastewater and oxidation-reduction potential of the waste water.

* * * * *